United States Patent
Mirsepassi et al.

(10) Patent No.: US 10,478,266 B2
(45) Date of Patent: Nov. 19, 2019

(54) ILLUMINATED SURGICAL PROBE HAVING MULTIPLE OPTICAL FIBERS

(71) Applicant: Novartis AG, Basel (CH)

(72) Inventors: Alireza Mirsepassi, Irvine, CA (US); Michael J. Papac, North Tustin, CA (US); Kambiz Parto, Laguna Niguel, CA (US)

(73) Assignee: Novartis AG, Basel (CH)

( * ) Notice: Subject to any disclaimer, the term of this patent is extended or adjusted under 35 U.S.C. 154(b) by 65 days.

(21) Appl. No.: 15/812,021

(22) Filed: Nov. 14, 2017

(65) Prior Publication Data

US 2018/0168768 A1 Jun. 21, 2018

Related U.S. Application Data

(60) Provisional application No. 62/434,494, filed on Dec. 15, 2016.

(51) Int. Cl.
*A61B 90/30* (2016.01)
*A61B 1/07* (2006.01)
(Continued)

(52) U.S. Cl.
CPC ............... *A61B 90/30* (2016.02); *A61B 1/07* (2013.01); *A61B 18/1477* (2013.01);
(Continued)

(58) Field of Classification Search
CPC ..... A61B 90/30; A61B 2090/306; A61B 1/07; A61B 18/1477; A61F 9/00; A61F 9/007
See application file for complete search history.

(56) References Cited

U.S. PATENT DOCUMENTS

| 5,201,730 A | 4/1993 | Easley et al. |
| 5,275,593 A | 1/1994 | Easley et al. |

(Continued)

FOREIGN PATENT DOCUMENTS

WO 2012012565 A2 1/2012

OTHER PUBLICATIONS

Paulo Ricardo Chaves De Oliveira, et al.; "Vitreoretinal instruments: vitrectomy cutters, endoillumination and wide-angle viewing systems", International Journal of Retina and Vitreous, vol. 2, No. 1, Dec. 1, 2016 (Dec. 1, 2016), XP055443185, DOI: 10.1186/s40942-016-0052-9 p. 9, col. 2, paragraph 3-5.
(Continued)

*Primary Examiner* — Julianna N Harvey
*Assistant Examiner* — Christina Negrellirodriguez

(57) ABSTRACT

A surgical probe system comprising a surgical probe having a probe needle, a first optical fiber incorporated onto the probe needle, wherein a distal end of the first optical fiber projects a first beam of illumination light over a tip of the probe needle when activated; a second optical fiber incorporated onto the probe needle, wherein a distal end of the second optical fiber projects a second beam of illumination light over the tip of the probe needle when activated; and a third optical fiber incorporated onto the probe needle, wherein a distal end of the third optical fiber projects a third beam of light over the tip of the probe needle to perform a distance measurement between the probe needle and a patient's when activated, wherein the distance measurement is displayed or audibly presented to aid a user in probe positional awareness with respect to the patient's retina.

12 Claims, 5 Drawing Sheets

Surgical Probe System 2a

Surgical Probe 10a

(51) Int. Cl.
*A61B 18/14* (2006.01)
*A61F 9/008* (2006.01)
*A61F 9/007* (2006.01)

(52) U.S. Cl.
CPC .......... *A61F 9/008* (2013.01); *A61F 9/00736* (2013.01); *A61B 2090/306* (2016.02); *A61F 2009/00844* (2013.01)

(56) References Cited

U.S. PATENT DOCUMENTS

| | | |
|---|---|---|
| 5,591,160 A | 1/1997 | Reynard |
| 5,651,783 A | 7/1997 | Reynard |
| 7,783,346 B2 | 8/2010 | Smith et al. |
| 8,968,347 B2 | 3/2015 | McCollam |
| 9,055,885 B2 | 6/2015 | Horvath et al. |
| 9,089,364 B2 | 7/2015 | Bhadri et al. |
| 9,364,982 B2 | 6/2016 | Schaller |
| 9,402,643 B2 | 8/2016 | Auld et al. |
| 9,561,085 B2 | 2/2017 | Yadlowsky et al. |
| 9,839,749 B2 | 12/2017 | Johnson et al. |
| 9,956,053 B2 | 5/2018 | Diao et al. |
| 10,016,248 B2 | 7/2018 | Mirsepassi et al. |
| 10,039,669 B2 | 8/2018 | Heeren |
| 10,278,785 B2 | 5/2019 | Mirsepassi et al. |
| 10,307,290 B2 | 6/2019 | Kern et al. |
| 2009/0161384 A1 | 6/2009 | Smith |
| 2009/0182313 A1 | 7/2009 | Auld |
| 2010/0228119 A1* | 9/2010 | Brennan .............. A61B 5/0066 600/424 |
| 2014/0121469 A1 | 5/2014 | Meckel et al. |
| 2015/0011839 A1 | 1/2015 | Auld et al. |
| 2016/0074212 A1 | 3/2016 | Price et al. |
| 2016/0228207 A1 | 8/2016 | Yadlowsky et al. |
| 2017/0014023 A1 | 1/2017 | Kern |
| 2017/0119491 A1 | 5/2017 | Mirsepassi et al. |
| 2017/0165114 A1 | 6/2017 | Hallen et al. |
| 2018/0055596 A1 | 3/2018 | Johnson |
| 2018/0132963 A1 | 5/2018 | Diao et al. |
| 2018/0133057 A1 | 5/2018 | Diao et al. |
| 2018/0168861 A1 | 6/2018 | Mirsepassi et al. |
| 2018/0338776 A1 | 11/2018 | Farley et al. |
| 2018/0338859 A1 | 11/2018 | Mirsepassi et al. |
| 2018/0338860 A1 | 11/2018 | Farley |

OTHER PUBLICATIONS

Chalam, et al., Illuminated Curved Vitrectomy Probe for Vitreoretinal Surgery, Ophthalmic Surgery, Lasers and Imaging, Nov./Dec. 2007—vol. 38 Â—Issue 6: 525-526.

Fisher et al., Inexpensive Illuminated Vitrectomy Cutter, The Journal of Retinal and Vitreous Diseases, Dec. 2003, vol. 23, Issue 6, p. 891.

Volpi International, The Universal Applicable Miniature Ringlight, Volpi International website, http://www.volpi.ch/htm/891/en/Miniature-Ringlight.htm; accessed Jun. 29, 2012, 2 pages.

* cited by examiner

Surgical Probe 10

ILLUMINATED SURGICAL PROBE HAVING MULTIPLE OPTICAL FIBERS

This application claims the benefit of priority of U.S. Provisional Patent Application Ser. No. 62/434,494 titled "Illuminated Surgical Probe Having Multiple Optical Fibers", filed on Dec. 15, 2016, whose inventors are Alireza Mirsepassi, Michael J. Papac and Kambiz Parto, which is hereby incorporated by reference in its entirety as though fully and completely set forth herein.

BACKGROUND

In ophthalmic surgery, a surgeon may typically use surgical apparatus comprising a vitreoretinal system with posterior segment and anterior segment procedure capabilities. The surgical apparatus may also include various probes, an ophthalmic microscope, an illuminator, a console with processors and a touch panel screen, and an embedded laser that is controlled from a system screen on the touch panel.

The types of probes used may include vitrectomy probes and laser probes. Vitrectomy probes may be used during vitreoretinal surgery to remove ocular tissues, such as vitreous humor and membranes covering the retina. These probes have a port for drawing in and dissecting tissues. A laser probe may have a continuous laser beam or a pulsed laser beam.

Some probe designs may include illumination that provides a narrow beam of light over the probe of sufficient intensity to facilitate vitreous visualization. However, the light beam can be too narrow and/or intense for certain tasks other than vitreous visualization. For example, the narrow beam may be too intense for general illumination in vitreous cavity or when the vitrectomy probe has to be operated very close to the retina for bi-manual surgery or other applications.

BRIEF SUMMARY

The exemplary embodiments provide methods and systems for a surgical probe system comprising a surgical probe having a probe needle, a first optical fiber incorporated onto the probe needle, wherein a distal end of the first optical fiber projects a first beam of illumination light over a tip of the probe needle when activated; a second optical fiber incorporated onto the probe needle, wherein a distal end of the second optical fiber projects a second beam of illumination light over a tip of the probe needle when activated; and a third optical fiber incorporated onto the probe needle, wherein a distal end of the third optical fiber projects a third beam of light over a tip of the probe needle to perform a distance measurement between the probe needle and a patient's retina when activated, wherein the distant measurement is displayed or audibly presented to aid a user in probe positional awareness with respect to the patient's retina.

According to the exemplary embodiments disclosed herein, an illuminated surgical probe is provided that expands the use of probes beyond vitrectomy and vitreous visualization. The Illuminated surgical probe having multiple optical fibers facilitates use of vitrectomy probes in bi-manual surgery where the vitrectomy probe has to operate close to the retina, as well as use for general illumination in a vitreous cavity.

DETAILED DESCRIPTION

The exemplary embodiment relates to an Illuminated surgical probe having multiple optical fibers. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the disclosure. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

Figure 1A:
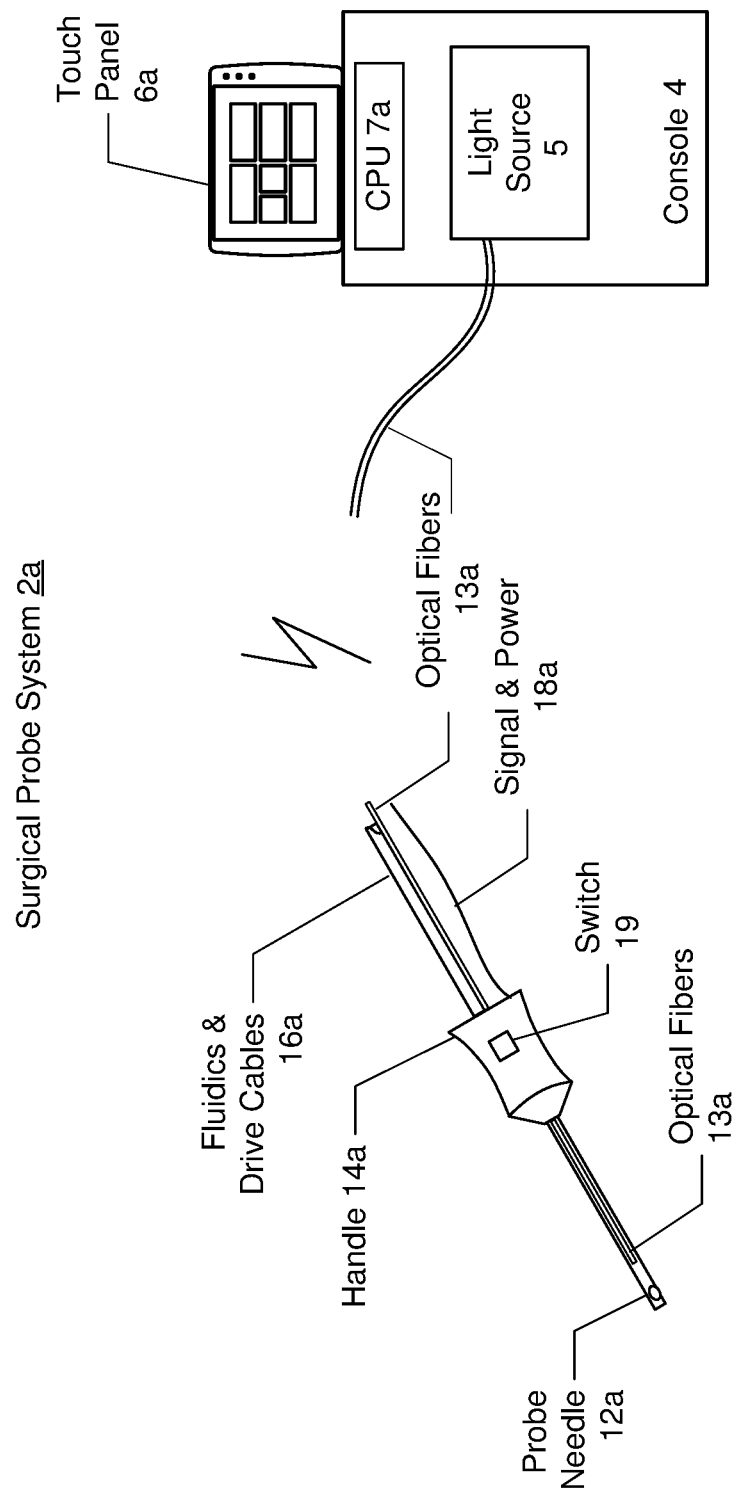
FIGS. 1A and 1B are diagrams illustrating embodiments of a surgical apparatus comprising an illuminated surgical probe having multiple optical fibers, where like components have like reference numerals.
Figure 1B:
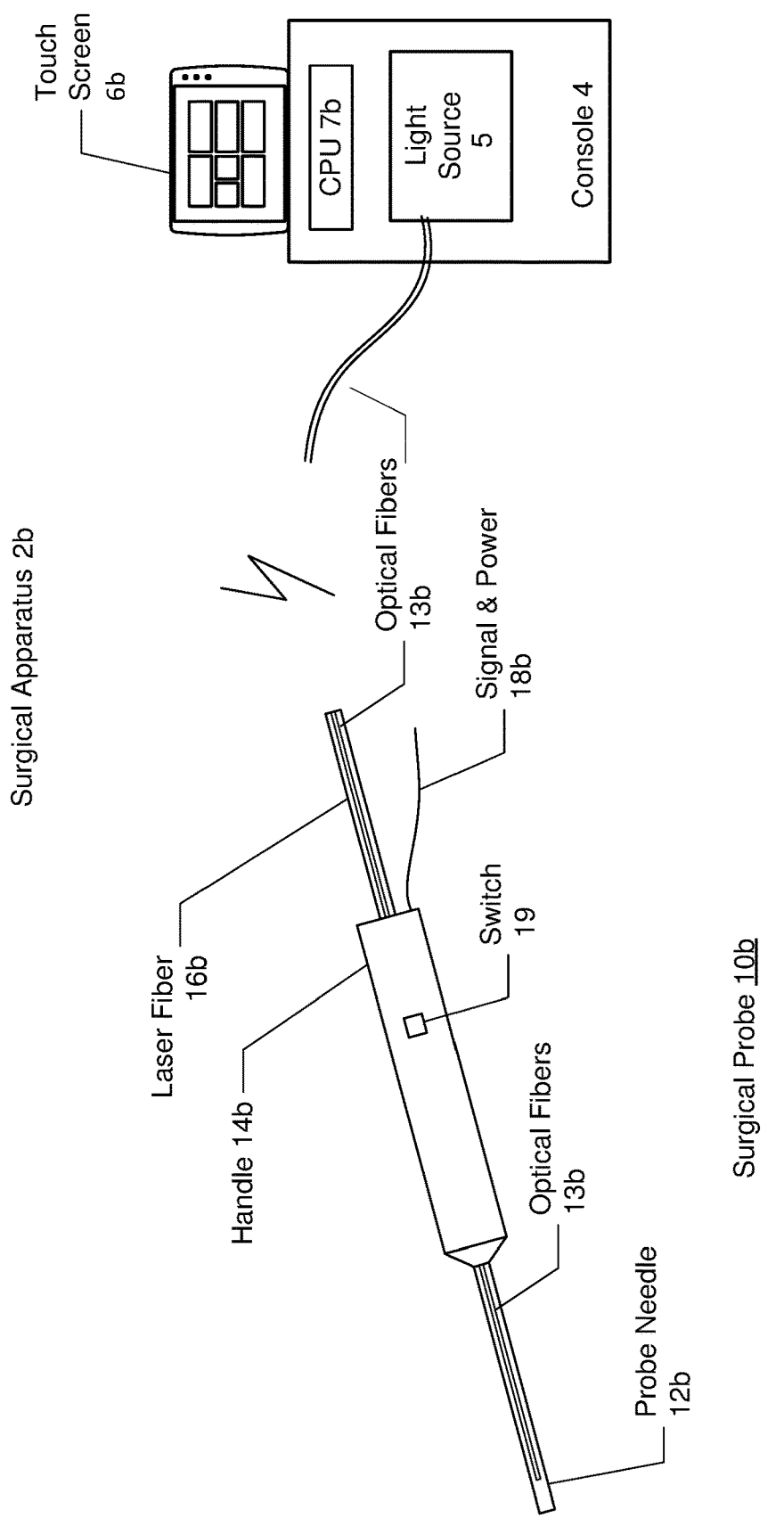

FIGS. 1A and 1B are diagrams illustrating embodiments of a surgical apparatus comprising an illuminated surgical probe having multiple optical fibers, where like components have like reference numerals. FIG. 1A shows an embodiment where the surgical probe system 2a includes a handheld surgical probe 10a coupled to console 4. In one embodiment, the surgical probe system 2a may represent a vitreoretinal system with posterior segment and anterior segment procedure capabilities. The console 4 of the surgical probe system 2a may include a light source (e.g., an illuminator) 5, a processor (e.g., CPU) 7a, and a touch panel 6a that may be used to control the console 4 and the surgical probe 10a. In an alternative embodiment, the light source may be located in the handle of the surgical probe.

The surgical probe 10a may comprise a vitrectomy probe that includes a probe needle 12a connected to a handle 14a, which in turn, is connected to fluidics and drive cables 16a and a signal and power line 18a, both coupled to the console 4. FIG. 1B shows an embodiment of a surgical probe system 2b where the surgical probe 10b comprises a laser probe, and similarly includes a probe needle 12b connected to a handle 14b, and the handle 14b connected to a laser fiber 16b and a signal and power line 18b.

According to one aspect of the exemplary embodiments, the surgical probe system 2a and 2b include multiple optical fibers 13a and 13b incorporated onto the probe needle 12a and 12b of the surgical probe 10a and 10b, respectively. Referring to both FIGS. 1A and 1B a proximal end of the optical fibers 13 are connected to the light source 5. A distal end of at least a portion of the optical fibers 13 projects illumination light from the light source 5 over a tip of the probe needle 12 when activated.

Figure 2A:
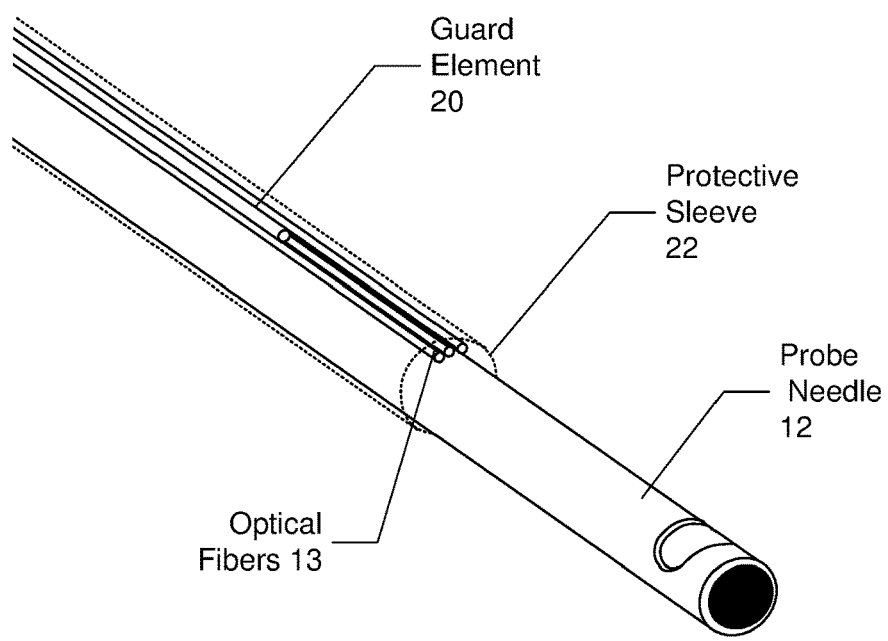
FIGS. 2A and 2B are diagrams illustrating multiple optical fibers incorporated into the surgical probe.
Figure 2B:
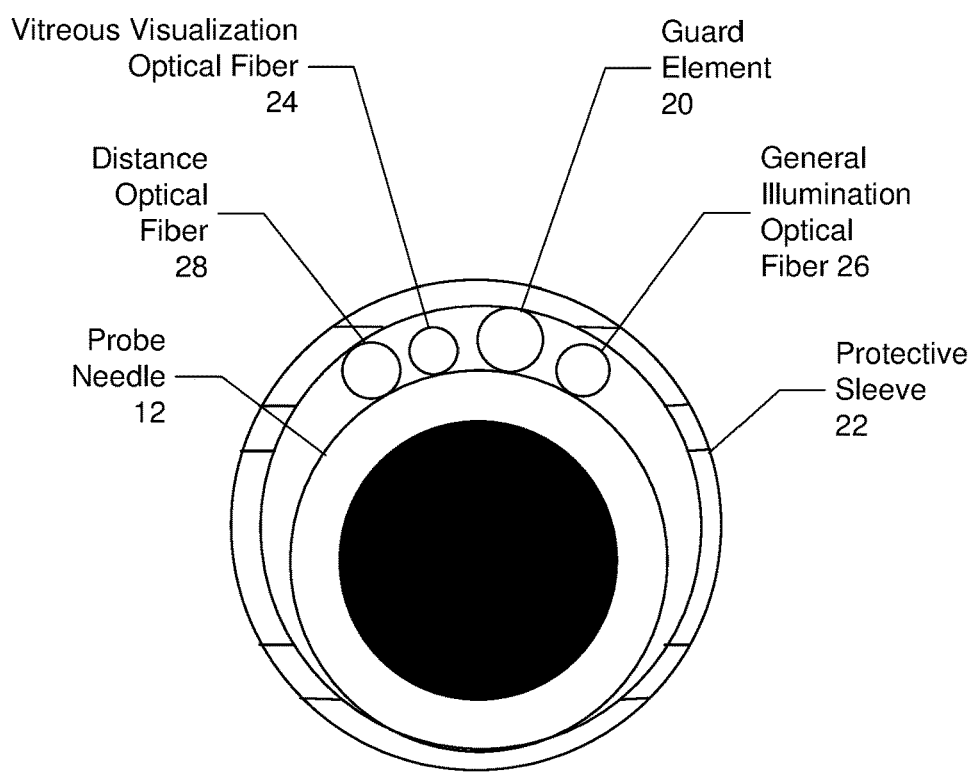

FIGS. 2A and 2B are diagrams illustrating multiple optical fibers incorporated into the surgical probe. FIG. 2A is a close-up view of the probe needle 12 showing multiple optical fibers incorporated thereon. An optional guard element 20 may be placed adjacent to the optical fibers 13 to support an optional protective sleeve 22. The protective sleeve 22 covers the optical fibers 13 and surrounds the portion of the surgical probe on which the optical fibers 13 lie. The function of the guard element 20 and the protective sleeve 22 is to provide support and prevent crushing of the optical fibers 13. In one embodiment, materials comprising one or both of the guard element 20 and the protective sleeve 22 may comprise any rigid material that supports and prevents crushing of the optical fibers 13. Example types of materials include stainless steel, glass, and the like. In one embodiment, the guard element 20 may be similar in shape to the optical fibers 13, but with a slightly larger diameter to bear the load from the protective sleeve 22.

FIG. 2B is a cross section of the probe needle and the optical fibers. In one embodiment, at least two of the optical fibers arranged on the surgical probe 10 function to provide illumination of the probe needle 12. More particularly, the optical fibers 13 may include a vitreous visualization optical fiber 24 that projects a narrow beam of illumination light over a tip of the probe needle 12 when activated, and a general illumination optical fiber 26 that projects a wide beam of illumination light over the tip of the probe needle 12 when activated.

According to a further aspect of the exemplary embodiment, the optical fibers 13 may further include a distance optical fiber 28 that projects a third beam of light over the tip of the probe needle 12 to perform a distance measurement between the probe needle and a patient's retina when activated, wherein the distant measurement may be displayed on the touch screen 6b or audibly presented to aid a user/surgeon in positional awareness of the surgical probe with respect to the patient's retina. In one embodiment, techniques such as interferometry can be used for the distance measurement. Thus, a Michelson interferometer or other type of optical interferometry may be used.

Although only the vitreous visualization optical fiber 24, the general illumination optical fiber 26, and distance optical fiber 28 are shown, it should be understood that any number of optical fibers can be incorporated as required per surgical probe functionality requirements.

According to a further aspect of the exemplary embodiments, the surgical probe 10 can be toggled between a narrow beam of illumination produced by the vitreous visualization optical fiber 24 and a wide beam of illumination produced by the general illumination optical fiber 26 either automatically based on the distance measurement and/or manually by a user (e.g., a surgeon or nurse/aid).

Figure 3A:
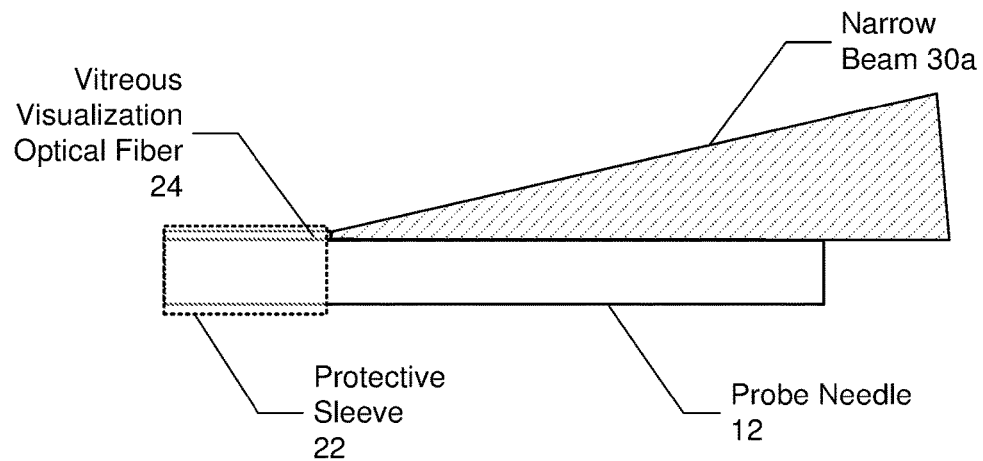
FIGS. 3A and 3B are diagrams illustrating first and second beams projected from the optical fibers.
Figure 3B:
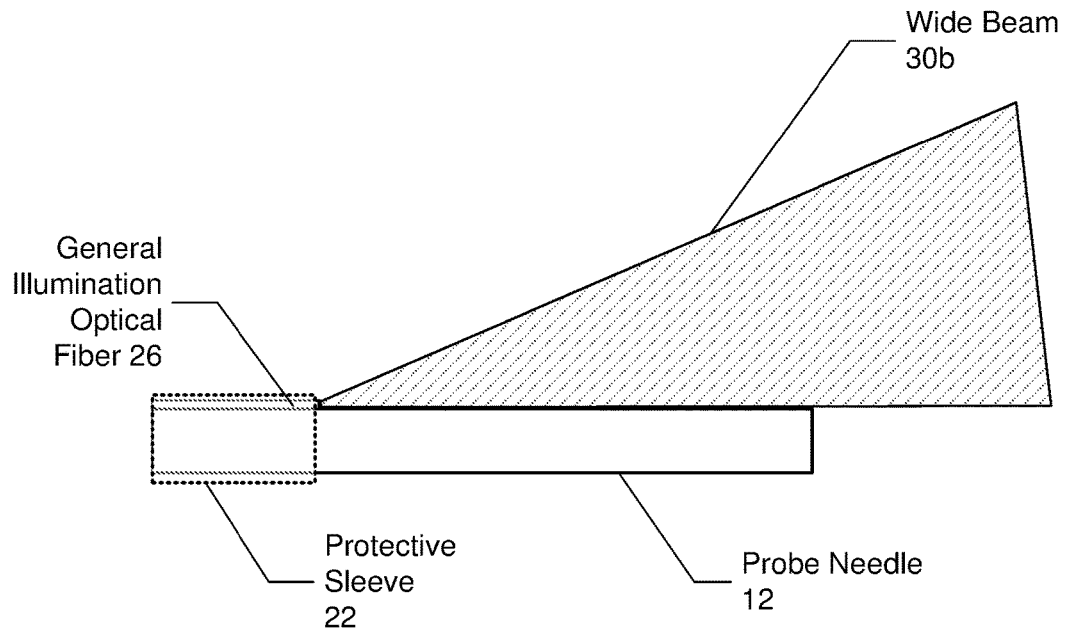

FIGS. 3A and 3B are diagrams illustrating first and second beams projected from the optical fibers. FIG. 3A shows activation of the vitreous visualization optical fiber 24 so that a narrow beam 30a of light with adequate intensity is delivered into the vitreous cavity for vitreous visualization. In one embodiment, the numerical aperture of the narrow beam has a low numerical value of approximately less than or equal to 0.3, or more specifically 0.1 to 0.3. In one specific application, the numerical aperture of the narrow beam may be 0.26.

FIG. 3B shows activation of the general illumination optical fiber 26 so that a wide beam 20b is delivered into the vitreous cavity for general illumination (background illumination or task illumination, e.g., such as for membrane peeling). In one embodiment, the numerical aperture of the wide beam has a relatively high numerical value of approximately greater than 0.3, or more specifically 0.4 to 0.7. In one specific application, the numerical aperture of the wide beam may be 0.56. In one embodiment, the light launched into both optical fibers 24 and 26 can be white light, a single wavelength (such as green light centered at 532 nm), RGB (Red Green Blue), or RGB plus additional wavelengths.

According to one aspect of the exemplary embodiments, the processor (CPU (Central processing unit)) 7a and 7b (FIGS. 1A and 1B, collectively processor 7) may automatically provide background/situational awareness illumination by toggling activation of the vitreous visualization optical fiber 24 and the general illumination optical fiber 26.

More specifically, based on the distance measurement, the processor may automatically toggle the illumination light between the narrow beam 30a having a first numerical aperture that facilitates vitreous visualization, and the wide beam 30b having a second numerical aperture that facilitates background illumination, where the second numerical aperture is larger than the first numerical aperture. For example, the processor 7 may be configured to compare a current distance measurement from the distance optical fiber 28 to a predetermined threshold distance. Responsive to determining that the current distance measurement is greater than or equal to the predetermined threshold distance, the processor may activate the vitreous visualization optical fiber 24 to produce the narrow beam 30a for vitreous visualization. Responsive to determining that the current distance measurement is less than the predetermined threshold distance, the processor may activate the general illumination optical fiber 26 to produce the wide beam 30b.

Referring again to FIGS. 1A and 1B, in another embodiment, activation of the vitreous visualization optical fiber 24 and the general illumination optical fiber 26 may be toggled manually. In one manual approach, the processor (CPU) 7 may be configured to toggle between activation of the vitreous visualization optical fiber 24 (narrow beam 30a) and the general illumination optical fiber 26 (wide beam 30b) based on commands entered at the console 4 (e.g., through touch screen 6 or a foot pedal) to which the surgical probe 10 is connected. In another manual approach, a switch 19 on the surgical probe 10 may be used by the user to switch between the two beams 30a and 30b. In one embodiment, the switch 19 may be located on the handle 14 of the surgical probe 10 and may comprise a two position switch, one position for the narrow beam 30a and a second position for the wide beam 30b. In one embodiment, the switch may be coupled to the console 4 by a wire. Other methods of switching are also contemplated (e.g., by voice from the surgeon, using a switch on the footpedal, etc.)

In yet another embodiment, activation of the vitreous visualization optical fiber 24 and the general illumination optical fiber 26 may be toggled manually by a user, but the processor is configured to automatically control intensity of the illumination light proportionally based on the distance measurement.

Figure 4:
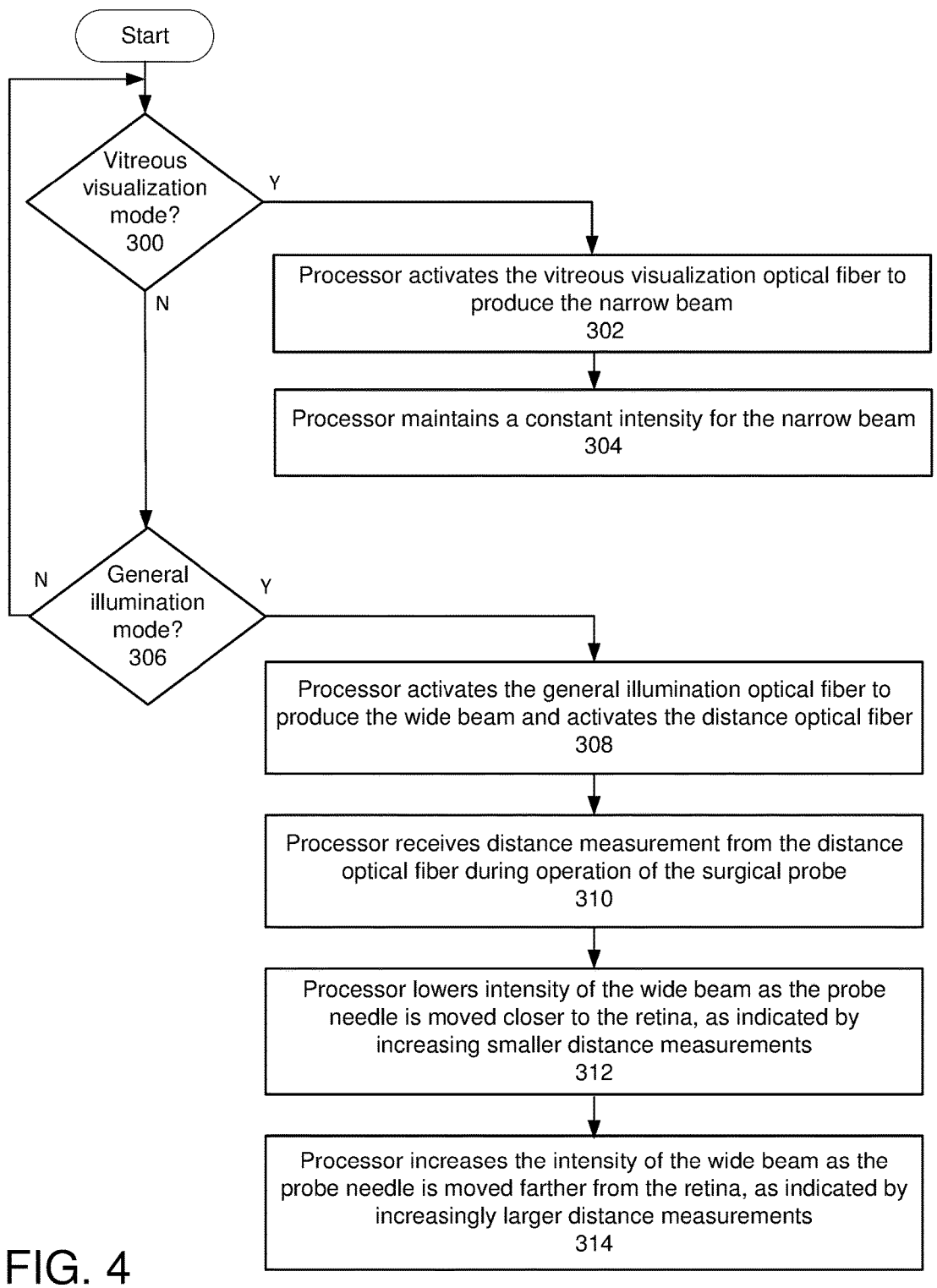
FIG. 4 is a flow diagram illustrating a process performed by the processor to automatically control intensity of illumination light on a surgical probe having optical fibers proportionally based on a distance measurement.

FIG. 4 is a flow diagram illustrating a process performed by the processor to automatically control intensity of illumination light on a surgical probe proportionally based on a distance measurement. The process may begin by the processor 7 determining whether vitreous visualization mode is activated (block 300). If the vitreous visualization mode is activated, the processor 7 activates the vitreous visualization optical fiber 24 to produce the narrow beam 30a (and deactivates the general illumination optical fiber 26 if activated) (block 302). The processor 7 maintains a constant intensity for the narrow beam and ignores or otherwise deactivates the distance optical fiber 28 (block 304).

If vitreous visualization mode is not activated (block 300) the processor 7 determines whether general illumination mode is activated (block 306). If so, the processor 7 activates the general illumination optical fiber 26 to produce the wide beam 30b and activates the distance optical fiber 28 (and deactivates the vitreous visualization optical fiber 24 if activated) (block 308).

The processor 7 receives the distance measurement from the distance optical fiber 28 during operation of the surgical probe 12 (block 310). In one embodiment, the processor 7 may receive distance measurements continuously, or may receive the distance measurements periodically.

The processor 7 lowers intensity of the wide beam 30b as the probe needle 12 is moved closer to the retina, as indicated by increasingly smaller distance measurements (block 312). Similarly, the processor increases the intensity of the wide beam 30b as the probe needle 12 is moved farther from the retina, as indicated by increasingly larger distance measurements (block 314). This may be performed, for example, by a table lookup approach where the lookup table contains distance and intensity level value pairs. The processor may look up current distance measurements in the table and adjust the intensity of the wide beam 30 to match the corresponding intensity level in the table. The process continues with the processor 7 monitoring for a manual change of modes.

In an exemplary embodiment, the processor 7 is located in the console 4. However, in another embodiment, the processor used to toggle the activation of the optical fibers 24 and 26 may be located within the surgical probe 10. In the embodiment where the processor is located within the surgical probe 10, a memory may be coupled to both the processor and/or the switch 19 in the surgical probe 10. The memory may be used to store the software instructions, as well as the distance measurement data collected from the distance optical fiber 28, and the data computed by the processor.

The processors 7 may be configured to execute the instructions stored in a memory to cause and control the process as described in this disclosure. As used herein, a processor may comprise one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality.

A method and system for an illuminated surgical probe having multiple optical fibers has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Accordingly, many modifications may be made by one of ordinary skill in the art without departing from the spirit and scope of the appended claims.

We claim:

1. An illuminated surgical probe system, comprising:
   a surgical probe having a probe needle;
   a first optical fiber incorporated onto the probe needle, wherein a distal end of the first optical fiber projects a first beam of illumination light over a tip of the probe needle when activated;
   a second optical fiber incorporated onto the probe needle, wherein a distal end of the second optical fiber projects a second beam of illumination light over the tip of the probe needle when activated;
   a third optical fiber incorporated onto the probe needle, wherein a distal end of the third optical fiber projects a third beam of light over the tip of the probe needle to perform a distance measurement between the probe needle and a patient's retina when activated, wherein the distance measurement is displayed or audibly presented to aid a user in positional awareness of the probe needle with respect to the patient's retina; and
   a processor that, based on the distance measurement, automatically toggles the illumination light between the first beam having a first numerical aperture that facilitates vitreous visualization and the second beam having a second numerical aperture that facilitates background illumination, wherein the second numerical aperture is larger than the first numerical aperture.

2. The surgical probe system as in claim 1, wherein the first numerical aperture has a numerical value of approximately less than or equal to 0.3.

3. The surgical probe system as in claim 1, wherein the second numerical aperture has a numerical value of approximately greater than 0.3.

4. The surgical probe system as in claim 1, wherein the processor is configured to:
   compare a current distance measurement to a predetermined threshold distance;
   responsive to determining that the current distance measurement is greater than or equal to the predetermined threshold distance, activate the first beam of illumination comprising a narrow beam of illumination; and
   responsive to determining that the current distance measurement is less than the predetermined threshold distance, activate the second beam of illumination comprising a wide beam of illumination.

5. The surgical probe system as in claim 1, wherein the surgical probe comprises a vitrectomy probe or a laser probe.

6. An illuminated surgical probe system, comprising:
   a surgical probe having a probe needle;
   a first optical fiber incorporated onto the probe needle, wherein a distal end of the first optical fiber projects a first beam of illumination light over a tip of the probe needle when activated;
   a second optical fiber incorporated onto the probe needle, wherein a distal end of the second optical fiber projects a second beam of illumination light over the tip of the probe needle when activated, wherein activation of the first optical fiber and the second optical fiber is toggled manually by the user;
   a third optical fiber incorporated onto the probe needle, wherein a distal end of the third optical fiber projects a third beam of light over the tip of the probe needle to perform a distance measurement between the probe needle and a patient's retina when activated, wherein the distance measurement is displayed or audibly presented to aid a user in positional awareness of the probe needle with respect to the patient's retina; and a processor configured to automatically control intensity of the illumination light proportionally based on the distance measurement;

wherein the processor is configured to:

responsive to determining a general illumination mode is activated, activate the second optical fiber to produce a wide beam;

receive the distance measurement from the third optical fiber during operation of the surgical probe;

lower intensity of the wide beam as a probe needle of the surgical probe is moved closer to a retina, as indicated by increasingly smaller distance measurements; and increase the intensity of the wide beam as the probe needle is moved farther from the retina, as indicated by increasingly larger distance measurements.

7. A computer-implemented method of providing an illuminated surgical probe, the surgical probe comprising a probe needle, the method comprising:

incorporating a first optical fiber onto the probe needle, wherein a distal end of the first optical fiber projects a first beam of illumination light over a tip of the probe needle when activated;

incorporating a second optical fiber incorporated onto the probe needle, wherein a distal end of the second optical fiber projects a second beam of illumination light over the tip of the probe needle when activated; and incorporating a third optical fiber onto the probe needle, wherein a distal end of the third optical fiber projects a third beam of light over the tip of the probe needle to perform a distance measurement between the probe needle and a patient's retina when activated, wherein the distance measurement is displayed or audibly presented to aid a user in positional awareness of the probe needle with respect to the patient's retina;

based on the distance measurement, automatically toggling by a processor, the illumination light between the first beam having a first numerical aperture that facilitates vitreous visualization and the second beam having a second numerical aperture that facilitates background illumination, wherein the second numerical aperture is larger than the first numerical aperture.

8. The method as in claim 7, wherein the first numerical aperture has a numerical value of approximately less than or equal to 0.3.

9. The method as in claim 7, wherein the second numerical aperture has a numerical value of approximately greater than 0.3.

10. The method as in claim 7, further comprising:

comparing, by the processor, a current distance measurement to a predetermined threshold distance;

responsive to the processor determining that the current distance measurement is greater than or equal to the predetermined threshold distance, activating the first beam of illumination comprising a narrow beam of illumination; and responsive to the processor determining that the current distance measurement is less than the predetermined threshold distance, activating the second beam of illumination comprising a wide beam of illumination.

11. The method as in claim 7, wherein the surgical probe comprises a vitrectomy probe or a laser probe.

12. A computer-implemented method of providing an illuminated surgical probe, the surgical probe comprising a probe needle, the method comprising:

incorporating a first optical fiber onto the probe needle, wherein a distal end of the first optical fiber projects a first beam of illumination light over a tip of the probe needle when activated;

incorporating a second optical fiber incorporated onto the probe needle, wherein a distal end of the second optical fiber projects a second beam of illumination light over the tip of the probe needle when activated, wherein activation of the first optical fiber and the second optical fiber is toggled manually by the user; and incorporating a third optical fiber onto the probe needle, wherein a distal end of the third optical fiber projects a third beam of light over the tip of the probe needle to perform a distance measurement between the probe needle and a patient's retina when activated, wherein the distance measurement is displayed or audibly presented to aid a user in positional awareness of the probe needle with respect to the patient's retina;

automatically controlling, by a processor, intensity of the illumination light proportionally based on the distance measurement;

responsive to the processor determining a general illumination mode is activated, activating the second optical fiber to produce a wide beam;

receiving the distance measurement by the processor from the third optical fiber during operation of the surgical probe;

lowering intensity, by the processor, of the wide beam as a probe needle of the surgical probe is moved closer to a retina, as indicated by increasingly smaller distance measurements; and increasing the intensity, by the processor, of the wide beam as the probe needle is moved farther from the retina, as indicated by increasingly larger distance measurements.

* * * * *